(12) United States Patent
Li (10) Patent No.: US 7,446,304 B2
(45) Date of Patent: Nov. 4, 2008

(54) DETECTION OF COLLISIONS IN MEDICAL PROCEDURES

(75) Inventor: Jonathan Li, Winnipeg (CA)

(73) Assignee: IMRIS, Winnipeg, Manitoba (CA)

( * ) Notice: Subject to any disclaimer, the term of this patent is extended or adjusted under 35 U.S.C. 154(b) by 47 days.

(21) Appl. No.: 11/397,910

(22) Filed: Apr. 5, 2006

(65) Prior Publication Data

US 2007/0228264 A1 Oct. 4, 2007

Related U.S. Application Data (60) Provisional application No. 60/786,400, filed on Mar. 28, 2006.

(51) Int. Cl.
*G01J 1/42* (2006.01)
*H05G 1/54* (2006.01)
(52) U.S. Cl. .......................... 250/227.14; 250/227.16; 250/370.1; 378/117; 600/424; 385/13
(58) Field of Classification Search ..................
250/227.14–227.16, 363.03, 370.1, 370.09; 378/95, 117, 177, 197; 385/12, 13; 600/407, 600/410, 415, 424
See application file for complete search history.

(56) References Cited

U.S. PATENT DOCUMENTS

| 5,105,455 | A | * | 4/1992 | Kato et al. ................. 378/117 |
|---|---|---|---|---|
| 5,411,023 | A | | 5/1995 | Morris et al. |
| 5,735,278 | A | | 4/1998 | Hoult et al. |
| 5,805,658 | A | * | 9/1998 | Hum et al. ..................... 378/4 |
| 6,144,790 | A | | 11/2000 | Bledin |
| 6,788,295 | B1 | * | 9/2004 | Inkster ....................... 345/175 |
| 2003/0107376 | A1 | * | 6/2003 | Yasuhara .................... 324/318 |
| 2004/0111025 | A1 | | 6/2004 | Avniash et al. |
| 2005/0220407 | A1 | | 10/2005 | Behrmann et al. |

FOREIGN PATENT DOCUMENTS

WO WO2005/099578 10/2007

* cited by examiner

*Primary Examiner*—Kevin Pyo
(74) *Attorney, Agent, or Firm*—Adrian D. Battison; Ade & Company Inc.

(57) ABSTRACT

A method of detecting collisions between elements in a medical procedure such as between a magnet and another element in the procedure mounting on the medical device a flexible body within which is mounted one or more parallel side by side optical fibers arranged such that the impact causes bending of one or more of the optical fibers and detecting changes in light transmission through the optical fiber to detect the bending and thus the collision. The single fiber or fibers are located in a junction between a lower body of resilient foam and a surface layer of a stiffer flexible material.

10 Claims, 6 Drawing Sheets

DETECTION OF COLLISIONS IN MEDICAL PROCEDURES

This application claims the benefit of priority under 35 U.S.C. 119 from Provisional Application, Ser. No. 60/786,400 filed Mar. 28, 2006.

This invention relates to a method and a device for detecting collisions in medical procedures such as in a MR imaging systems, surgical robot systems and the like where mechanical devices are movable in the procedure with the risk of impact.

BACKGROUND OF THE INVENTION

In U.S. Pat. No. 5,735,278 (Houllt et al) issued Apr. 7, 1998, is disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients. The system is used as follows:

The magnet is at first some distance from the operating table, either in the side or back of the surgical room or perhaps within a holding bay area. When imaging is required, the MRI magnet is advanced from its holding area and positioned in the imaging position over the table. Images are taken and magnet is retracted to its holding area.

Thus the MRI system consists of a magnet, rails, installed on the site, and a magnet mover system, which consists of a magnet carriage, cable carrier, and mover control system.

The system is installed in renovated hospital buildings or in new buildings. The system can be installed in one-room or two-room configurations, and may be useable in the future in multi-room configurations. In the two-room configuration, the magnet and MRI system is shared between the two rooms as needed by the hospital staff, leading to increased cost effectiveness within the business case.

For patient and surgical team safety, it is important to have collision detection and anti-collision products attached to the magnet, in order to stop the magnet from moving if collision is detected. Several patents have previously discussed anti-collision methods and technologies for medical devices, with these patents coming from GE, Philips and Hitachi. None of these approaches can be used within MRI systems, because of the magnetic and RF field requirements within the MRI system. None of the previous patents discusses the use of fiber-optics to provide collision detection.

SUMMARY OF THE INVENTION

It is one object of the invention to provide an impact detection device which is particularly suitable in a medical procedure and a method for detecting such collisions.

According to one aspect of the invention there is provided a method of detecting collisions between equipment elements in a medical procedure comprising:

providing a medical device which is related to a second object in the procedure such that relative movement may occur in the medical procedure;

mounting on either the medical device or the second object a detection device responsive to impacts between the medical device and the second object;

the detection device comprising a flexible body within which is mounted at least one optical fiber arranged such that the impact causes bending of the optical fiber;

and detecting changes in light transmission through the at least one optical fiber to detect the bending and thus the collision.

One instance of this invention uses a fiber bundle in which a plurality of fibers are arranged in an array.

Preferably the fibers in the array are generally side by side.

Preferably the fibers in the array are generally parallel.

Preferably the fibers in the array are buried beneath a surface of the flexible body.

Preferably the flexible body includes an under layer which is resilient and a surface layer which is stiffer than the under layer.

Preferably the at least one fiber is located at a junction between the layers.

Preferably the medical device comprises a magnet for use in magnetic resonance imaging.

Preferably the flexible body is mounted on the magnet.

Preferably the flexible body is generally annular and is located on an annular end of the magnet.

Preferably the magnet has a bore with longitudinal ribs in the bore of the magnet and wherein the flexible body includes projections matching the ribs in the bore.

Preferably the at least one fiber is bent so as to project into the projections.

Preferably the flexible body defines an end face at the end of the magnet and wherein the flexible body includes an end face layer and under body with the at least one fiber being located within the body.

Preferably the end face layer is stiffer than the under body layer and the at least one fiber is located at a junction between the layers.

According to a second aspect of the invention there is provided an impact detection device comprising:

a flexible body arranged to be mounted on an object expected to be involved in an impact;

at least one optical fiber arranged such that the impact causes bending of the optical fiber;

and a sensing system for detecting changes in light transmission through the at least one optical fiber to detect the bending and thus the collision.

The arrangement defined above can be arranged to overcome a number of problems and to provide a number of features necessary to effectively implement an MR compatible collision detection system, as follows:

The system components can not interfere with the homogeneity of the magnet.

The system components have to be MR compatible.

The sensing technology can not be affected by the magnetic field.

The system needs to communicate with the magnet mover control system.

The human interface has to be cleanable with standard hospital cleaners.

The system has to be capable of being calibrated to allow for surgical draping being pulled across it without delivering a false detection.

The unique nature of the sensing technology described herein allows the system to effectively guard non-symmetrical and non-uniform shapes. This is a limitation with standard IR light guarding technologies. Their limitations include straight line guarding, locating a transmitter and receiver pair at the guarding perimeter, and require some amount of electrical current for transmission and detection.

The design possesses a fiber optic cable sensor strategically placed and embedded into a low density foam layer. This is then covered on top with a higher density foam layer. The sensing technology can use different techniques for detecting the bending of the optical fiber but one example operates on the principal of light intensity differential. When the normal intensity is established, disturbing the fiber optic sensor cable causes distortions in the light intensity. This can be detected at the output of the fiber optic sensor cable which is interpreted as a trigger. The high density foam layer serves as a broad spectrum/load distributing trigger to the fiber optic sensor cable below. The low density foam acts as a compression layer to softly cushion the object detected as the magnet mover comes to an aggressive stop.

Traditional sensors utilize some form of electrical, mechanical or electromechanical technology. Our design is unique in that there are no electrical, mechanical or electromechanical components at the guarding perimeter. The use of fiber optic technology to detect collisions in our application is suitable for the following reasons:

There are no metallic components at the guard perimeter and therefore has zero effect on the magnet shim.

The fiber optic cable and foam layers are MR compatible.

The sensing technology is not affected by the magnetic field.

The collision detection controller effectively communicates to the magnet mover controller that a collision was detected. The magnet mover controller takes this information and acts upon it.

The foam surface is coated with a cleanable protective coating that has been tested for chemical and organic resistance.

The controller calibration range includes the detection of the slightest contact (e.g. surgical draping that is pulled across the foam) all the way to hardest contact (e.g. Impact with fixed operating room table or skull frame).

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
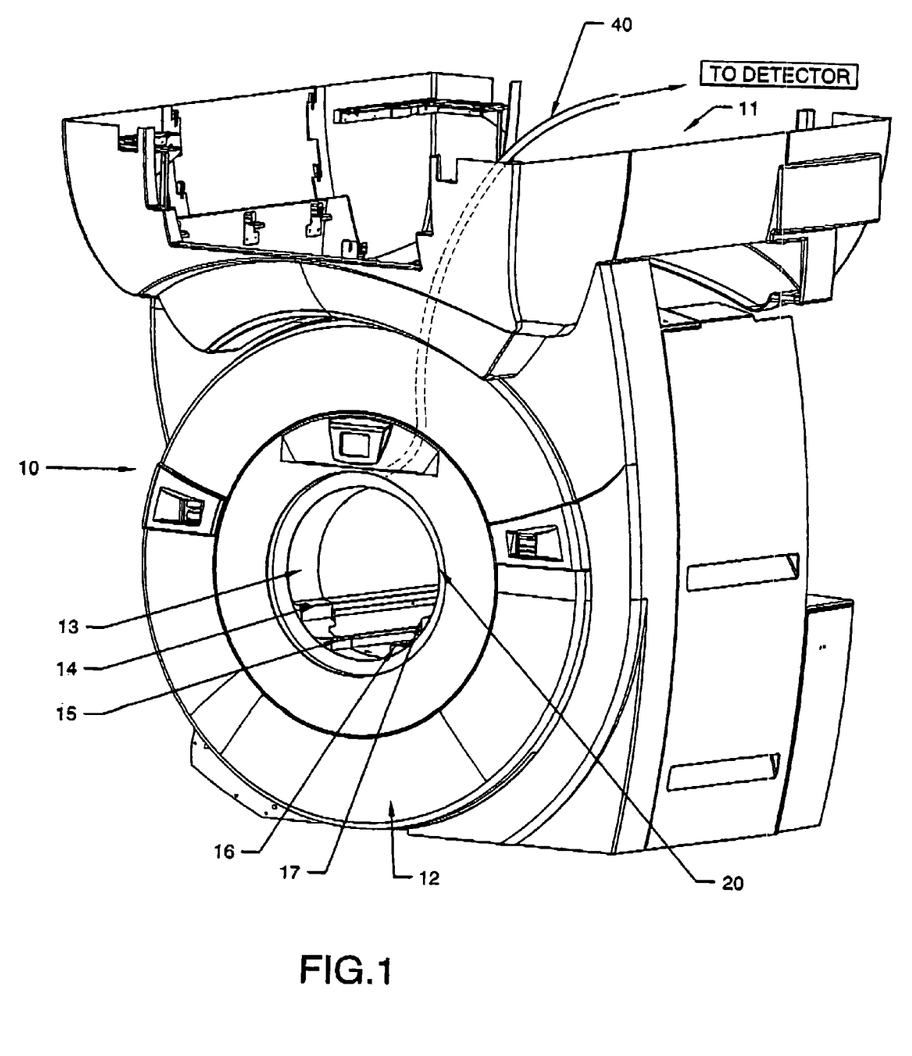
FIG. 1 is an isometric view of a magnet for use in magnetic resonance imaging with an impact sensing system attached to a forward end of the magnet.

In FIG. 1 is shown an isometric view of a magnet 10 of the type generally indicated in the above U.S. Pat. No. 5,735,278. The magnet is supported on a support system 11 for movement relative to the patient table and other components of the system which are not shown in FIG. 1 but further details of which can be obtained from the above US patent. The magnet 10 includes a magnet winding 12 defining a cylindrical bore 13 into which the object to be imaged is inserted. In the example shown, the bore 13 is horizontal with a horizontal axis with a magnet being mounted for movement along the axis. The bore includes 4 ribs 14, 15, 16 and 17 which extend parallel to the axis and project inwardly from the cylindrical bore toward the axis. These ribs are provided for co-operation with the patient table.

The magnet is of a conventional nature and includes further details well known to a person skilled in the art which will not be described herein since these details are not relevant to the present invention.

The magnet may include shielding layers in the form of fabric which is attached to the magnet and can be placed over the end of the magnet to assist in shielding from extraneous electro magnetic radiations.

A device for detecting impacts is mounted on the end of the magnet as indicated at 20. This device is shown in more detail in FIGS. 2 through 6.

Figure 2:
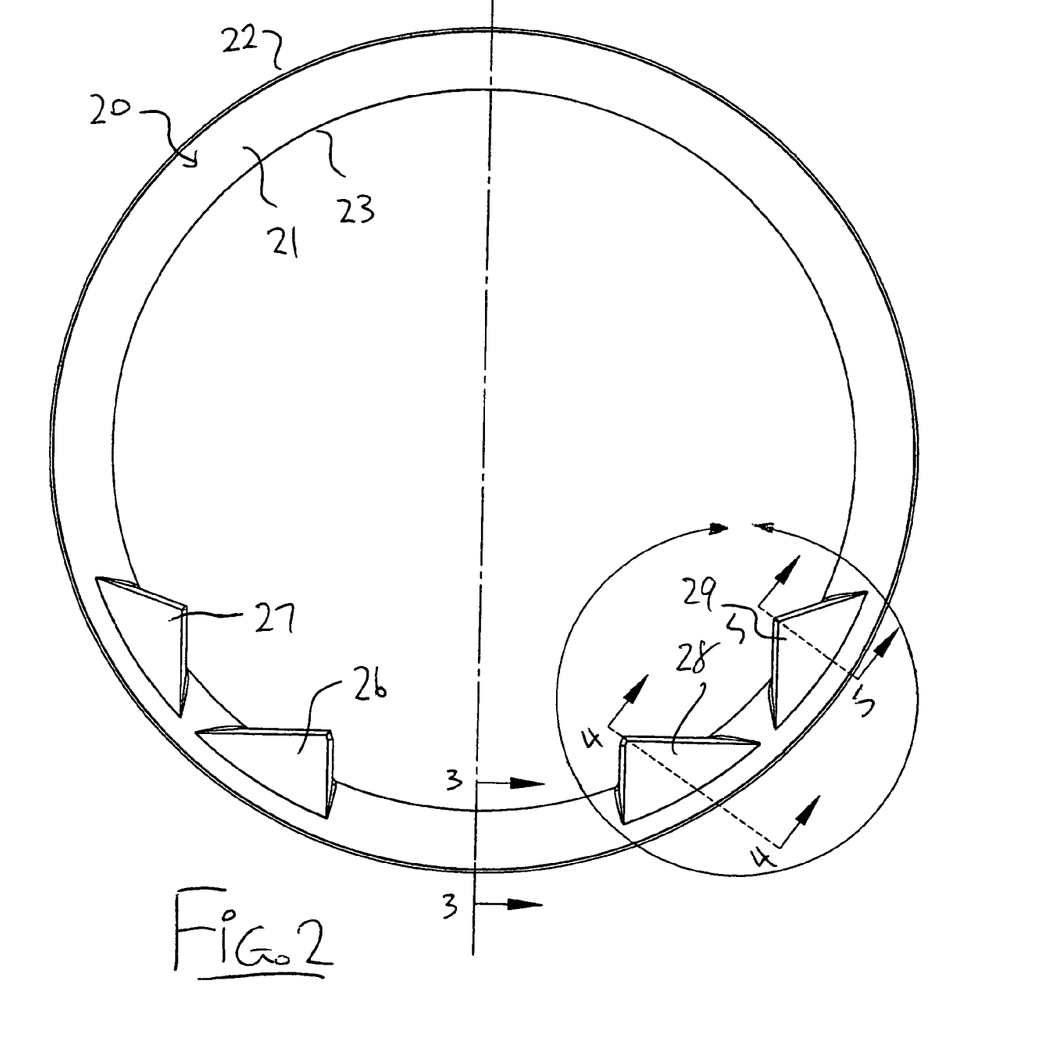
FIG. 2 is a front elevational view of the impact sensing system of FIG. 1.

The device 20 comprises a ring 21 having an outer edge 22 and an inner edge 23. The ring has a front face 24 for facing outwardly from the end of the magnet and a rear face 25 which is fastened to the end of the magnet. Thus the ring surrounds the bore with the inside edge 23 lying in a common cylindrical surface with an inside surface of the bore. The outside edge 22 is spaced outwardly from this surface a distance sufficient to ensure that impacts of the magnet with components at or within the bore impact firstly upon the detecting device 20.

The detecting device 20 includes inwardly projecting portions 26, 27, 28 and 29 which match the shape and location of the ribs on the bore of the magnet. Thus these elements form a covering also over the ribs. As best shown in the cross sections of FIGS. 3, 4 and 5, the ring 21 is formed from a resilient body 30 which is formed of an inner layer 31 and an outer layer 32. The outer layer 32 is relatively thin. Both layers are formed from a resilient foam material with the outer layer 32 being stiffer than the inner layer. Thus an impact with the outer layer 32 tends to deform the inner layer 31 and move the outer layer 32 relative to the inner layer.

The thickness and the stiffness of the two layers also influence the sensitivity of the impact detection and the area over which the detection can be monitored. For example, if the outer layer is very stiff, then a small point impact on any part of the outer layer will cause a larger deflection of the fiber or fibers in the inner softer layer, leading to a larger change in the intensity of light within the fiber or fibers. The stiff outer layer therefore provides large intensity changes with impact, but poor spatial resolution of impact. If the outer layer is very soft, however, the spatial resolution can be made very accurate (because the outer layer doesn't affect a large amount of fiber or number of fibers) but the change in light intensity is less. By modifying the thickness of the various layers, differing impact sensitivities can be achieved. If the designer wants to avoid small impacts but wants to detect impacts of greater force, then the layers should be thicker. With thinner layers, the smaller force impacts are also detected but the resolution between larger and smaller impacts becomes less. The sensitivity of the impact detection can also be adjusted through software calibration of the intensity levels that are detected, and through changing the foam type to achieve different stiffness properties. If an array of fibers is used, it is possible to control the spacing of the fiber array such that larger or more pointy impacts can be detected. Obviously, it is also possible to use an array of fibers, with the fibers in the neighbourhood of the impact all being affected, and with software and detection systems being used to calculate the size and location of the impact. Obviously, multiple arrays of fibers could be used, with different arrays being positioned within different portions of the potential impact area, and therefore if a given array indicated a collision, the location of the impact would be known as well. Obviously, different spatial organizations of the fiber sensor pads can also be made. For example, if one wishes to protect a square surface, a foam sensor pad, perhaps with adhesive on the back, can be attached to the square surface, at least one fiber would enter and exit the foam pad, and the foam sensor pad would therefore indicate whether an impact is found on that surface. This approach can be useful for microscopes and other equipment that may be used within the operating room when the magnet is affecting the room.

Figure 6:
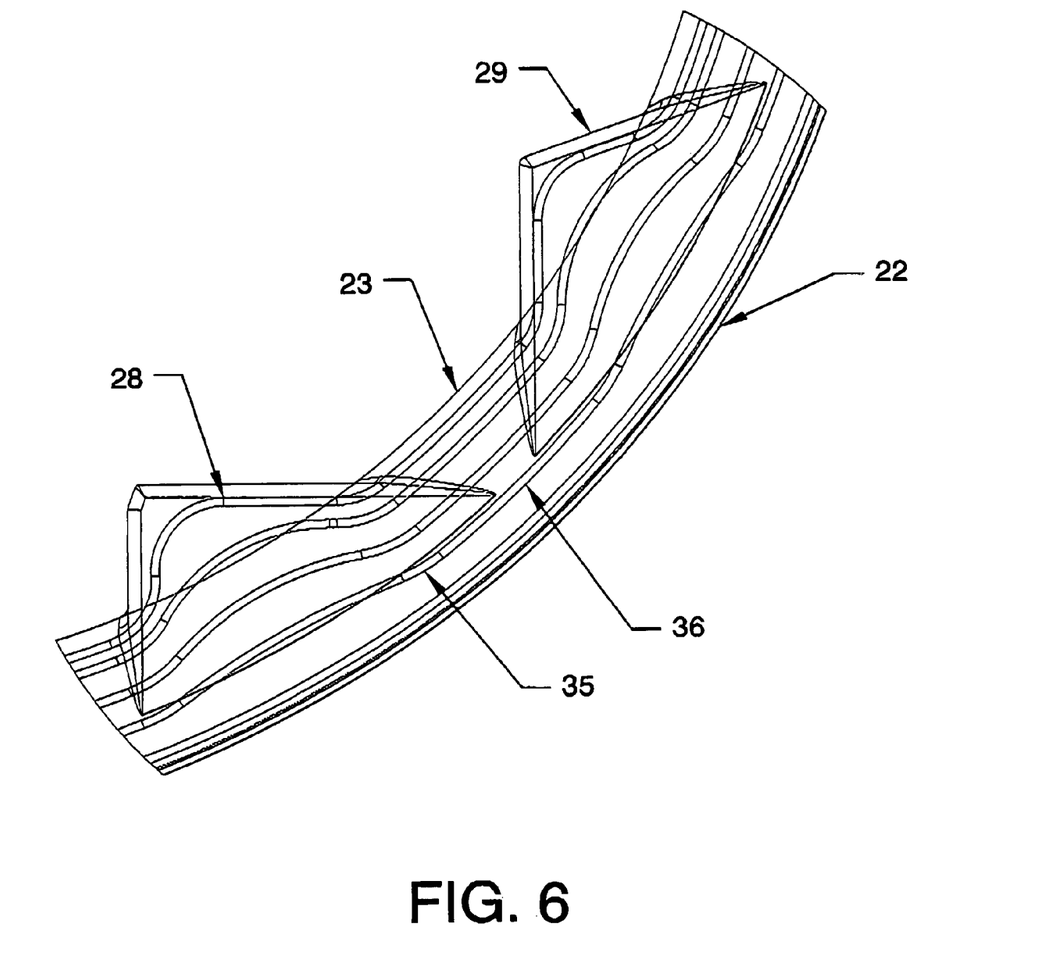
FIG. 6 is a cross sectional view taken along the lines 6-6 of FIG. 4.

At the junction between the two layers is provided an array of optical fibers 35. The array is generally indicated at 36 and includes, as best shown in FIG. 6, a series of the fibres 35 arranged around the ring in generally parallel equidistantly spaced relationship. In the embodiment shown there are four such fibres. The fibres lie in a circle concentric with the axis of the ring with the fibres being spaced from the outside edge 22 and from the inside edge 23 and generally equidistantly spaced therebetween. However the fibres are also distorted so that they bend into the ribs or projections 28 and 29 on one side and also into the projections 26 and 27 on the other side.

Each of the fibres is continuous and extends around the full periphery of the ring. In the case where only one fiber is used, there is one entry fiber and one exit fiber. The fibres emerge from the ring through a bundle of the fibres as indicated at 40 with the bundle passing through the mounting system with other electronic components of the system to the electronic control systems which are generally located in the room adjacent to but separate from the magnet.

The detector is of a known construction which provides a light source which is injected into the fibre at one end of the fibre so that the light source defines a beam within the fibre that passes along the fibre and emerges either from the transmitting end or an opposed end where the is located a light sensor.

Various known techniques are available for detecting bending of the fibre. These can utilize the characteristics of the light for example the polarization or the intensity or the intensity within a certain polarization so as to sense bending of the fibre.

The detector provides a threshold value which can be adjusted so as to vary the sensitivity of the system to impact.

Figure 3:
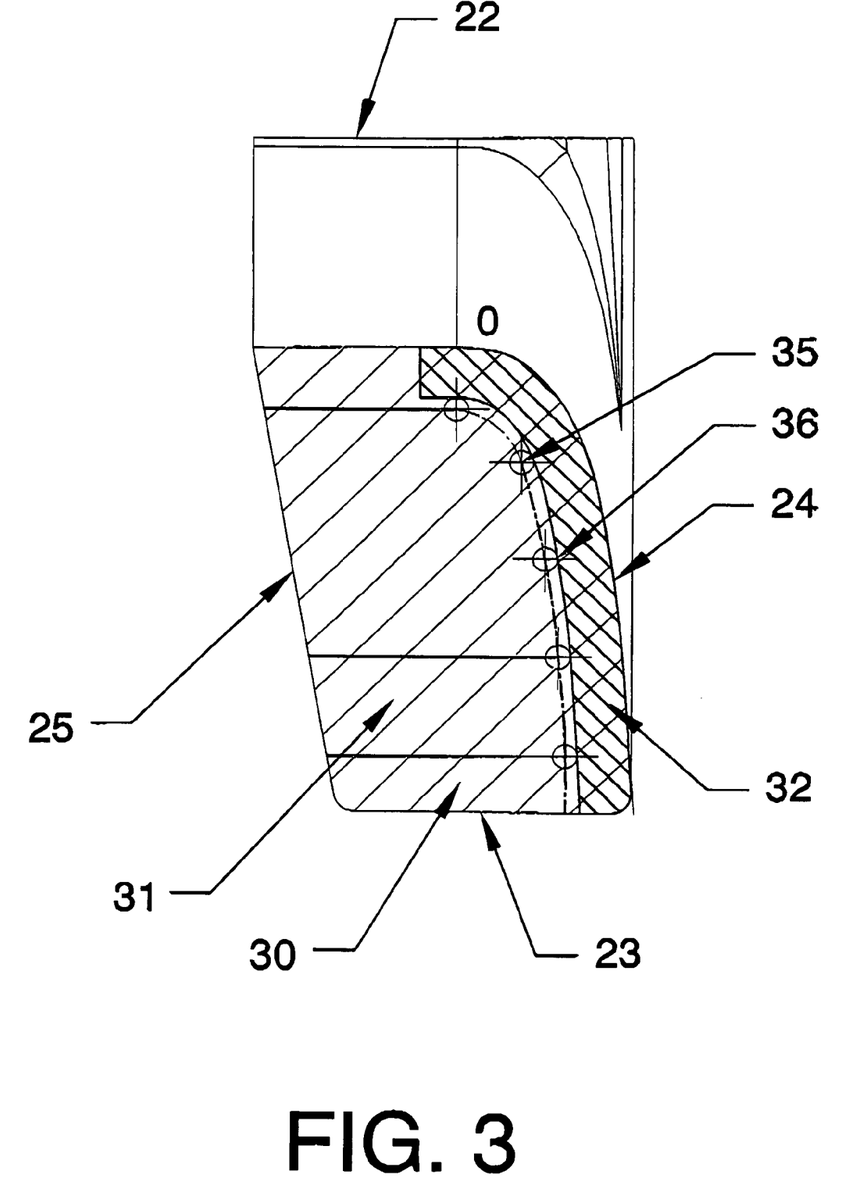
FIGS. 3, 4 and 5 are cross sectional views taken along the lines 3-3, 4-4 and 5-5 respectively of FIG. 2.
Figure 4:
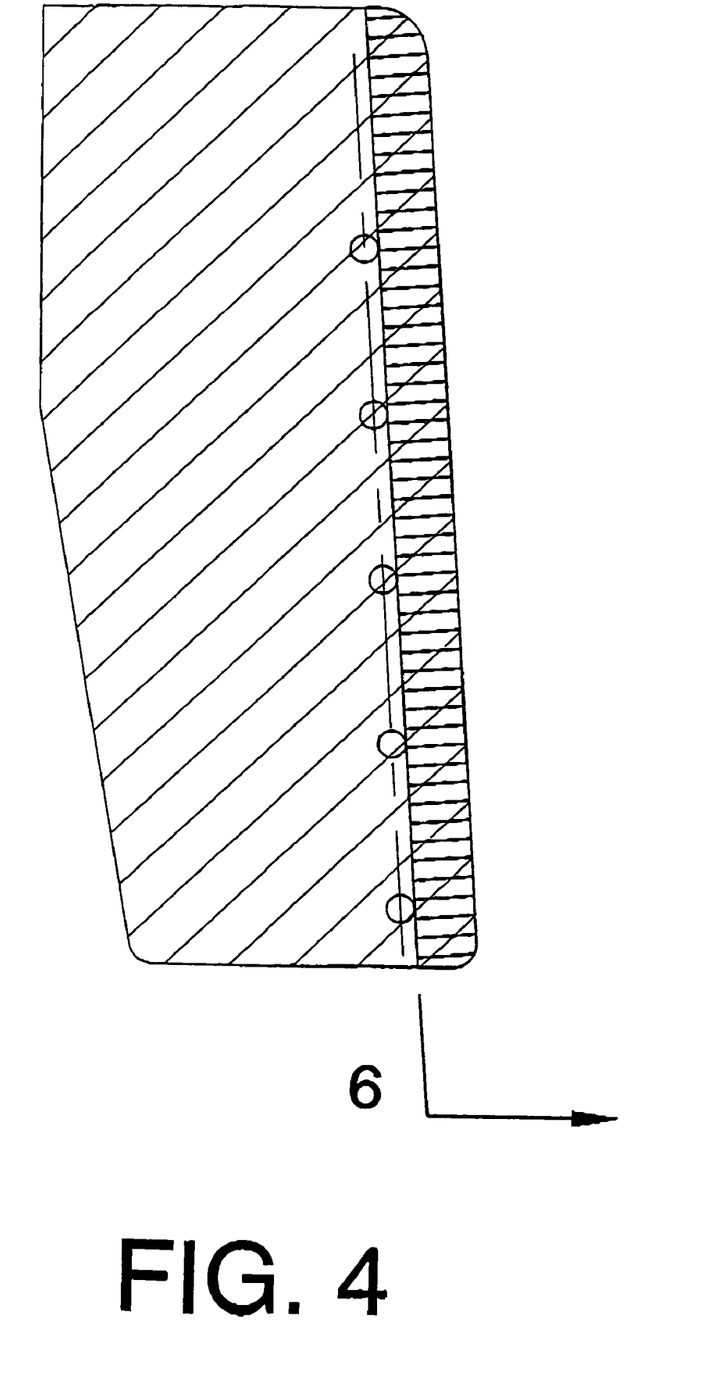
Figure 5:
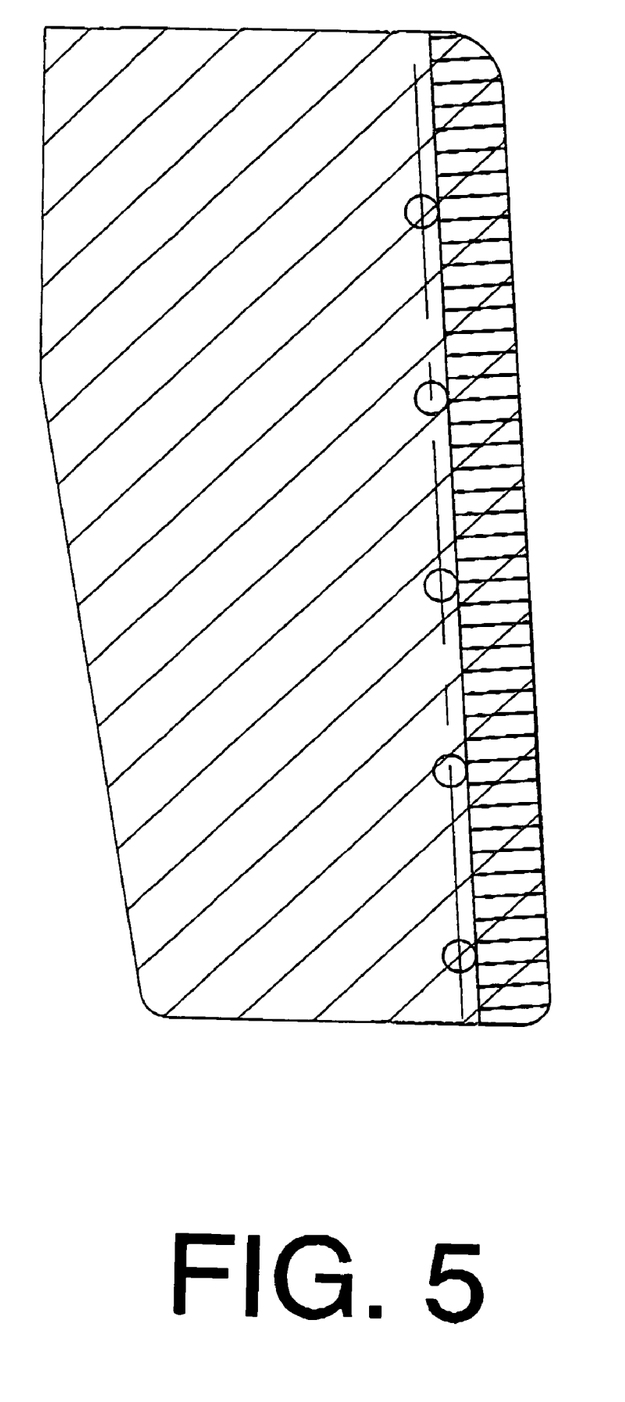

The system can also be varied to accommodate different levels of impact by selection of the materials for the layers 31 and 32. It will be appreciated that a reduction in the stiffness of the layer 31 will allow the layer 32 to move more easily and under less force.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of detecting collisions between a medical device and a second object in a medical procedure comprising:
   wherein the medical device comprises a magnet for use in magnetic resonance imaging, the magnet having a cylindrical bore surrounding a longitudinal axis of the magnet and an end face lying in a radial plane of the longitudinal axis;
   wherein the magnet is movable along its longitudinal axis in a direction toward and away from the second object;
   mounting on the magnet a detection device responsive to impacts between the magnet and the second object;
   the detection device comprising a flexible body within which is mounted at least one optical fiber arranged such that the impact causes bending of the optical fiber;
   and detecting changes in light transmission through the at least one optical fiber to detect the bending and thus the collision;
   wherein the flexible body is a ring attached to the radial end face of the magnet with an end face of the ring being parallel to the end face of the magnet, an inner face of the ring being located in a common cylindrical surface with the bore and an outer edge of the ring spaced outwardly of the bore and inwardly of an outer edge of the end face of the magnet.

2. The method according to claim 1 wherein the cylindrical bore has protrusions projecting generally radially inwardly and wherein the flexible body includes projections thereon projecting generally radially inwardly and matching the protrusions in the bore.

3. The method according to claim 2 wherein at least one part of the at least one fiber is bent so as to project into the projections for detecting impact on the projections.

4. The method according to claim 1 wherein the flexible body includes a first layer of a first compressible flexible foam material with a rear surface of the first layer attached to the end face of the magnet and a front surface of the first layer spaced from the rear surface thereof, wherein the flexible body includes a second layer of a second compressible flexible foam material having a rear surface of the second layer in contact with the front surface of the first layer and a front surface of the second layer spaced from the rear surface of the second layer, wherein the second layer is stiffer than the first layer and wherein the at least one fiber is located at a junction between the first and second layers.

5. An impact detection device comprising:
   a flexible body arranged to be mounted on an object expected to be involved in an impact;
   at least one optical fiber arranged such that the impact causes bending of the optical fiber;
   and a sensing system for detecting changes in light transmission through the at least one optical fiber to detect the bending and thus the collision;
   wherein the flexible body includes a contact surface arranged to be mounted on a face of the object;
   wherein the flexible body includes a first layer of a first compressible flexible foam material with a rear surface of the first layer at the contact surface and a front surface of the first layer spaced from the rear surface thereof;
   wherein the flexible body includes a second layer of a second compressible flexible foam material having a rear surface of the second layer in contact with the front surface of the first layer and a front surface of the second layer spaced from the rear surface of the second layer;
   wherein the second layer is stiffer than the first layer;
   and wherein the at least one fiber is located at a junction between the first and second layers.

6. A method of detecting collisions between a medical device and a second object in a medical procedure comprising:
   wherein the medical device comprises a magnet for use in magnetic resonance imaging, the magnet having a cylindrical bore surrounding a longitudinal axis of the magnet and an end face lying in a radial plane of the longitudinal axis;
   wherein the magnet is movable along its longitudinal axis in a direction toward and away from the second object;
   mounting on the magnet a detection device responsive to impacts between the magnet and the second object;
   the detection device comprising a flexible body within which is mounted at least one optical fiber arranged such that the impact causes bending of the optical fiber;

and detecting changes in light transmission through the at least one optical fiber to detect the bending and thus the collision;

wherein the magnet has at least one element projecting generally radially inwardly from the cylindrical bore;

and wherein the flexible body is mounted on the end face surrounding the bore and includes an inner edge of the flexible body located in a common cylindrical surface with the bore with at least one projection thereon projecting radially inwardly from the inner edge and matching the inwardly projecting element of the magnet.

7. The method according to claim 6 wherein at least one part of the at least one fiber is bent so as to project into the at least one projection for detecting impact on the at least one projection.

8. The method according to claim 6 wherein the flexible body includes a first layer of a first compressible flexible foam material with a rear surface of the first layer attached to the end face of the magnet and a front surface of the first layer spaced from the rear surface thereof, wherein the flexible body includes a second layer of a second compressible flexible foam material having a rear surface of the second layer in contact with the front surface of the first layer and a front surface of the second layer spaced from the rear surface of the second layer, wherein the second layer is stiffer than the first layer and wherein the at least one fiber is located at a junction between the first and second layers.

9. A method of detecting collisions between a medical device and a second object in a medical procedure comprising:

wherein the medical device comprises a magnet for use in magnetic resonance imaging, the magnet having a cylindrical bore surrounding a longitudinal axis of the magnet and an end face lying in a radial plane of the longitudinal axis;

wherein the magnet is movable along its longitudinal axis in a direction toward and away from the second object;

mounting on the magnet a detection device responsive to impacts between the magnet and the second object;

the detection device comprising a flexible body within which is mounted at least one optical fiber arranged such that the impact causes bending of the optical fiber;

and detecting changes in light transmission through the at least one optical fiber to detect the bending and thus the collision;

wherein the flexible body is mounted on the end face of the magnet;

wherein the flexible body includes a first layer of a first compressible flexible foam material with a rear surface of the first layer at the end face of the magnet and a front surface of the first layer spaced from the rear surface thereof;

wherein the flexible body includes a second layer of a second compressible flexible foam material having a rear surface of the second layer in contact with the front surface of the first layer and a front surface of the second layer spaced from the rear surface of the second layer;

wherein the second layer is stiffer than the first layer;

and wherein the at least one fiber is located at a junction between the first and second layers.

10. An impact detection device for detecting impacts with a magnet for use in magnetic resonance imaging, the magnet having a cylindrical bore surrounding a longitudinal axis of the magnet and an end face lying in a radial plane of the longitudinal axis, the device comprising:

a flexible body arranged to be mounted on an the end face of the magnet;

at least one optical fiber in the flexible body arranged such that impact causes bending of the optical fiber;

and a sensing system for detecting changes in light transmission through the at least one optical fiber to detect the bending and thus the collision;

wherein the flexible body is annular so as to surround the bore with a circular inner edge of the flexible body arranged to be located in a common cylindrical surface with the bore;

wherein the flexible body has at least one projection thereon projecting radially inwardly from the inner edge;

and wherein at least one part of the at least one fiber is bent so as to project into the at least one projection for detecting impact on the projection.

* * * * *